United States Patent
Zheng et al.

(10) Patent No.: US 10,782,379 B2
(45) Date of Patent: *Sep. 22, 2020

(54) METHOD, APPARATUS, AND DEVICE FOR MAGNETIC RESONANCE CHEMICAL SHIFT ENCODING IMAGING

(71) Applicant: SHENZHEN INSTITUTES OF ADVANCED TECHNOLOGY CHINESE ACADEMY OF SCIENCES, Shenzhen (CN)

(72) Inventors: Hairong Zheng, Shenzhen (CN); Xin Liu, Shenzhen (CN); Chuanli Cheng, Shenzhen (CN); Chao Zou, Shenzhen (CN)

(73) Assignee: SHENZHEN INSTITUTES OF ADVANCES TECHNOLOGY CHINESE ACADEMY OF SCIENCES, Shenzhen (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/645,798

(22) PCT Filed: Dec. 30, 2015

(86) PCT No.: PCT/CN2015/099966
§ 371 (c)(1),
(2) Date: Mar. 10, 2020

(87) PCT Pub. No.: WO2017/113233
PCT Pub. Date: Jul. 6, 2017

(65) Prior Publication Data
US 2020/0241099 A1    Jul. 30, 2020

(51) Int. Cl.
*G01R 33/565*    (2006.01)
*A61B 5/055*    (2006.01)

(52) U.S. Cl.
CPC ........ *G01R 33/56527* (2013.01); *A61B 5/055* (2013.01)

(58) Field of Classification Search
CPC .. A61B 5/055; G01R 33/443; G01R 33/4625; G01R 33/4828; G01R 33/485;
(Continued)

(56) References Cited

U.S. PATENT DOCUMENTS

| 6,459,922 B1 | 10/2002 | Zhang |
| 2002/0193680 A1* | 12/2002 | Feiweiler .............. A61B 5/4869 600/410 |
| 2005/0165296 A1 | 7/2005 | Ma et al. |

FOREIGN PATENT DOCUMENTS

| CN | 1385711 A | 12/2002 |
| CN | 102369454 A | 3/2012 |

(Continued)

OTHER PUBLICATIONS

Frank J. Rybicki, et al., Fast Three-Point Dixon MR Imaging of the Retrobulbar Space with Low-Resolution Images for Phase Correction: Comparison with Fast Spin-Echo Inversion Recovery Imaging, AJNR Am J Neuroradiol 22, Oct. 2001, pp. 1798-1802.

*Primary Examiner* — Rishi R Patel
(74) *Attorney, Agent, or Firm* — Bayramoglu Law Offices LLC

(57) ABSTRACT

A method, an apparatus, and a device for magnetic resonance chemical shift encoding imaging are provided. The method includes in a phasor-error spectrum established based on a simplified multi-point magnetic resonance signal model, determining a pixel point having a unique phase factor value and causing the phasor-error spectrum to reach a local minimum value as an initial seed point; estimating a phase factor value of a pixel point to be estimated according to the initial seed point to obtain a field map; mapping and merging the field maps at the highest resolution to obtain a (Continued)

reconstructed field map; determining a reconstructed seed point from the reconstructed field map, and estimating the reconstructed seed point to obtain a phase factor value of a reconstructed pixel point to be estimated.

19 Claims, 6 Drawing Sheets

(58) Field of Classification Search
CPC .............. G01R 33/56; G01R 33/5608; G01R 33/56527; G01R 33/56572
See application file for complete search history.

(56) References Cited

FOREIGN PATENT DOCUMENTS

| | | | |
|---|---|---|---|
| CN | 103140167 | A | 6/2013 |
| CN | 103608693 | A | 2/2014 |
| CN | 104382597 | A | 3/2015 |
| CN | 106908747 | A | 6/2017 |
| JP | H0284934 | A | 3/1990 |
| WO | 2006121827 | A2 | 11/2006 |
| WO | 2013130587 | A1 | 9/2013 |

* cited by examiner

METHOD, APPARATUS, AND DEVICE FOR MAGNETIC RESONANCE CHEMICAL SHIFT ENCODING IMAGING

CROSS REFERENCE TO THE RELATED APPLICATIONS

This application is the national phase entry of International Application No. PCT/CN2015/099966, filed on Dec. 30, 2015.

TECHNICAL FIELD

The present invention relates to a method, an apparatus, and a device for magnetic resonance chemical shift encoding imaging, and belongs to the technical field of magnetic resonance imaging.

BACKGROUND

Magnetic resonance chemical shift encoding imaging is an imaging method based on the difference in chemical shifts between components in the tissue. It is realized by collecting signals at different echo times and fitting a mixed signal model. The most commonly used chemical shift encoding imaging in clinical practice is water-fat separation imaging, which is mainly used in applications such as fat suppression and fat quantification. During the separation process, the local field of Bo can be corrected by multi-echo chemical shift encoding imaging, and images of pure water and pure fat can be obtained at the same time. However, in the case where the $B_0$ field is too large or the imaging tissue is spatially separated, the traditional multi-echo chemical shift encoding imaging tends to converge to an incorrect local minimum value when estimating a $B_0$ field deviation, which further causes a result of fat-water swapping.

The principle of multi-echo chemical shift encoding imaging is to assume that tissue signals are obtained by simultaneously exciting various components, and the chemical shift of each component with respect to water is known, and then mathematical models between the signals and each component, a $B_0$ field map, and echo time (TE) are fitted. The most commonly used chemical shift encoding imaging in practice is water-fat separation imaging, that is, the two components including water and fat are separated by multi-echo signals.

In the prior art, there is a two-point water-fat separation technique. In this technique, it is assumed that the field map is evenly distributed, two specific echo times are selected to separately collect the images of water and fat protons in the same and opposite phases, and a water map and a fat map are obtained by simple addition and/or subtraction operations. To solve the impact caused by the non-uniformity of the $B_0$ field, a three-point water-fat separation technique is further provided in the prior art, that is, based on the two-point water-fat separation technique, a third echo time is selected to collect an image of water and fat protons in opposite phases again. The disadvantage of this algorithm is that only water-fat signals can be separated, but water or fat signals cannot be identified. Besides, in the prior art, there is also an algorithm of iterative decomposition of water and fat with echo asymmetry and least squares estimation (IDEAL), which performs linearization processing on the above signal model, and then uses a least squares method to separately estimate the field map value and separate the water and fat components for each pixel in the image. However, the algorithm tends to converge to a local optimal solution when the Bo field has relatively large non-uniformity, and tends to obtain the result of water-fat swapping in the single-component pixels.

SUMMARY

To solve the problems in the existing method for chemical shift encoding imaging that two components are swapped due to the uneven distribution of the B0 field and only the signal with two components can be separated while neither of the components can be identified separately, the present invention provides a method, an apparatus and a device for a magnetic resonance chemical shift encoding imaging. Specifically, the following technical solutions are included:

A method for magnetic resonance chemical shift encoding imaging includes:

in a sample image at a predetermined resolution, establishing a phasor-error spectrum based on a simplified multi-point magnetic resonance signal model;

determining a pixel point having a unique phase factor value and causing the phasor-error spectrum to reach a local minimum value in the phasor-error spectrum as an initial seed point;

estimating a phase factor value of a pixel point to be estimated according to the initial seed point to obtain a field map at the predetermined resolution;

mapping a plurality of field maps at the predetermined resolution separately at the highest resolution to obtain a plurality of field maps at the highest resolution, and merging the plurality of field maps to obtain a reconstructed field map;

determining a reconstructed seed point in the reconstructed field map, and estimating based on the reconstructed seed point to obtain a phase factor value of a reconstructed pixel point to be estimated; and obtaining separate images of two predetermined components according to the phase factor values of the reconstructed seed point and the reconstructed pixel point to be estimated.

An apparatus for magnetic resonance chemical shift encoding imaging includes:

a phase error spectrum establishment module, configured for establishing a phasor-error spectrum based on a simplified multi-point magnetic resonance signal model in a sample image at a predetermined resolution;

a seed point selection module, configured for determining a pixel point having a unique phase factor value and causing the phasor-error spectrum to reach a local minimum value in the phasor-error spectrum as an initial seed point;

an estimation module, configured for estimating a phase factor value of a pixel point to be estimated according to the initial seed point to obtain a field map at the predetermined resolution;

a field map reconstruction module, configured for mapping a plurality of field maps at the predetermined resolution separately at the highest resolution to obtain a plurality of field maps at the highest resolution, and merging the plurality of field maps to obtain a reconstructed field map;

a phase factor determination module, configured for determining a reconstructed seed point from the reconstructed field map, and estimating based on the reconstructed seed point to obtain a phase factor value of a reconstructed pixel point to be estimated; and an imaging module, configured for obtaining separate images of two predetermined components according to the phase factor values of the reconstructed seed point and the reconstructed pixel point to be estimated.

The advantages of the present invention are as follows: the field map estimation is performed at multiple resolutions, an area simultaneously containing two components can be identified as a seed point at a low resolution, thus increasing the number and distribution range of seed points. Multiple high-resolution field maps are merged by using a self-checking mechanism, eliminating the deviation caused by a jump of the phase factor values at the highest resolution, and ensuring the correctness of selection of the final seed point, so that the signals of the two components can be accurately identified.

DETAILED DESCRIPTION OF THE EMBODIMENTS

Figure 1:
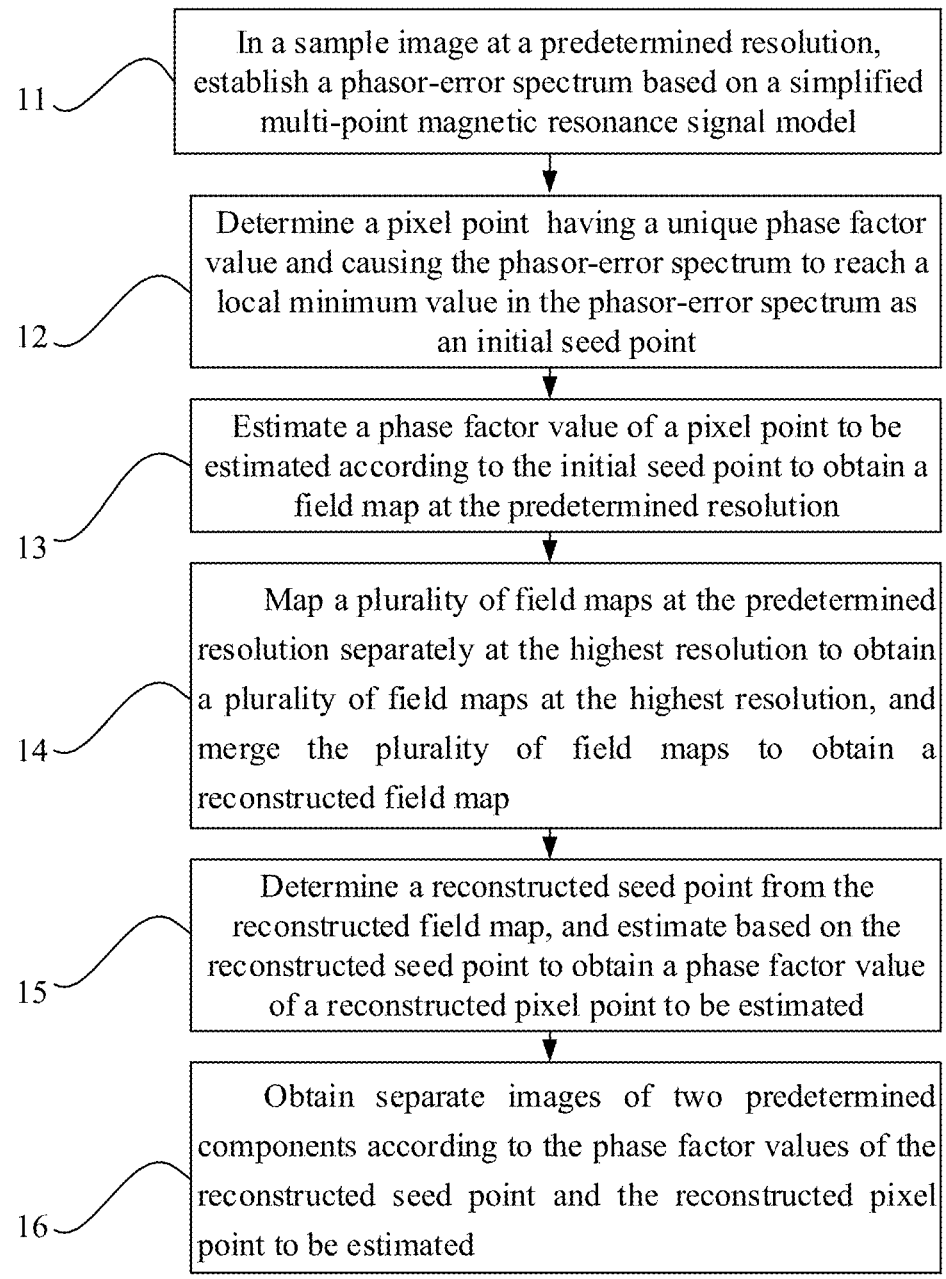
FIG. 1 shows a flowchart of a method for magnetic resonance chemical shift encoding imaging by way of example.

In the prior art, to accurately identify water and fat signals, researchers have proposed a variety of improved algorithms, which are mainly divided into three categories: the first category is to apply a global smoothing constraint on a field map, such as graph-cut algorithms and globally optimal surface estimation (GOOSE) algorithms, and the concept of graph cut is used to estimate the field map in this category; the second category is a local growth algorithm including selecting pixel points with high signal-to-noise ratios (SNR) and similar water-fat ratios as reasonable seed points and then selecting correct field map values of unestimated pixel points by a local growth algorithm according to the similarity between domain field maps; and the third category is a multi-resolution algorithm including first estimating a field map on a low-resolution image, then using a step-by-step optimization method to sequentially obtain field maps at higher resolutions and the highest resolution, and finally obtaining a water-fat separation image.

However, the above existing algorithms all have their shortcomings. For example, the graph-cut algorithms and GOOSE algorithms are invalid at isolated tissue, because the correct field map values cannot be transmitted to the isolated tissue, which results in relatively low computational efficiency of the graph-cut algorithms and GOOSE algorithms. Moreover, the existing local growth algorithm depends on the selection of seed points, where the incorrect seed points will lead to inaccurate separation results. This algorithm also depends on the number of seed points. It must be ensured that each isolated tissue contains at least one seed point. However, this algorithm can only find seed points on low-resolution field maps. For other isolated tissue, it will not be able to obtain correct field map values, thereby affecting the stability of the local growth algorithm. The existing multi-resolution algorithms all use multi-resolution strategies and there is a high correlation between different resolutions. The estimated initial value of the high-resolution field map depends too much on the value of the low-resolution field map. If the field map converges to one incorrect local extreme value at a low resolution or the actual field map between different resolutions changes drastically, then the above initial value will cause the high-level field map to converge to one incorrect minimum value as well, and this error is transmitted layer by layer to the highest resolution and amplified, leading to erroneous separation results.

For the above shortcomings, the present invention provides a method for chemical shift encoding imaging based on multi-resolution safest path local growth and a self-checking field map estimation algorithm to achieve correct field map estimation and separation of two components. In this method, the selection of the seed points and the local growth of the safest path are independently completed at different resolutions to ensure that enough seed points are obtained, thereby avoiding the incorrect transmission of the field map between different resolutions, then a self-checking mechanism is used to merge the field maps obtained at different resolutions to ensure the correctness of the final seed point, and finally, local growth is performed again to obtain the correct field map estimated values.

As shown in FIG. 1, the method for magnetic resonance chemical shift encoding imaging provided by the present invention includes:

Step 11, in a sample image at a predetermined resolution, establishing a phasor-error spectrum based on a simplified multi-point magnetic resonance signal model.

In this step, a two-dimensional original image may be low-pass filtered and under-sampled according to a pre-defined under-sampling coefficient to obtain two-dimensional original images at different low resolutions, and then a phasor-error spectrum of each pixel point in the two-dimensional original images at different low resolutions is obtained. A phase factor value that causes each pixel point to reach a local minimum value is determined according to the phasor-error spectrum.

Step 12, determining a pixel point having a unique phase factor value and causing the phasor-error spectrum to reach a local minimum value in the phasor-error spectrum as an initial seed point.

In this step, a phase factor value that causes each pixel point to reach a local minimum value is determined according to the phasor-error spectrum. If a signal-to-noise ratio of a pixel point is greater than a predetermined value and has the unique phase factor value, the pixel point may be determined as the seed point.

Optionally, the process of determining the pixel point having the unique phase factor value includes:

if the pixel point has only one local minimum value that causes the fitting error to be less than a predetermined value, then determining the local minimum value as the unique phase factor value of the pixel point.

Step 13, estimating a phase factor value of a pixel point to be estimated according to the initial seed point to obtain a field map at the predetermined resolution.

The process of estimating the phase factor value of the pixel point to be estimated includes:

if the pixel point to be estimated includes a plurality of local minimum values, determining local minimum values with a fitting error less than the predetermined value as a plurality of phase factor values of the pixel point to be estimated; and selecting a phase factor value having the maximum similarity to phase factor values of adjacent seed points from the plurality of phase factor values of the pixel point to be estimated as the phase factor value of the pixel point to be estimated.

Optionally, the process of determining the phase factor value of the pixel point to be estimated by the safest path local growth algorithm includes:

selecting a pixel point to be estimated with an amplitude greater than a first threshold value to establish a first pixel point set to be estimated;

obtaining a phase difference between two adjacent seed points of each pixel point to be estimated in the first pixel point set to be estimated, and selecting a pixel point to be estimated with the maximum phase difference less than a second threshold value to establish a second pixel point set to be estimated;

sorting pixel points to be estimated in the second pixel point set to be estimated in a descending order according to the number of the adjacent seed points, and selecting a predetermined number of pixel points to be estimated to establish a third pixel point set to be estimated;

obtaining the maximum phase similarity between a pixel point to be estimated in the third pixel set to be estimated and the adjacent seed points, and using a phase factor value of the pixel point to be estimated with the similarity greater than a third threshold value as the phase factor value of the pixel point to be estimated; and adding the pixel point to be estimated with the similarity greater than the third threshold value as a seed point to estimate the pixel point to be estimated in the first pixel point set to be estimated until the number of adjacent seed points of the pixel point to be estimated in the first pixel point set to be estimated is zero.

Optionally, in this step, the phase factor value of the pixel point to be estimated in the first pixel point set to be estimated may also be determined, and the process includes:

reducing the first threshold value by a predetermined amount to determine a fourth pixel point set to be estimated, and determining a phase factor value of a pixel point to be estimated in the fourth pixel point set to be estimated until the first threshold value is reduced to zero; and determining the phase factor value of the pixel point to be estimated in which the phase factor value has not been determined in the first pixel point set to be estimated as an average value of the phase factor values of the adjacent seed points.

Step 14, mapping a plurality of field maps at the predetermined resolution separately at the highest resolution to obtain a plurality of field maps at the highest resolution, and merging the plurality of field maps to obtain a reconstructed field map.

In the mapping, the field map at the highest resolution may be selected by using the field map at the predetermined resolution obtained in step 13 as an initial value, and the process may include:

obtaining phase similarity between all phase factor values of each reconstructed pixel point to be estimated at the highest resolution and a phase factor value of a corresponding pixel point at the predetermined resolution, and determining the phase factor value with the highest similarity as the phase factor value of the reconstructed pixel point to be estimated.

Step 15, determining a reconstructed seed point from the reconstructed field map, and estimating based on the reconstructed seed point to obtain a phase factor value of a reconstructed pixel point to be estimated.

The process of determining the phase factor value of the reconstructed pixel point to be estimated may include:

if the reconstructed pixel point to be estimated has the same phase factor value in all field maps, then determining the reconstructed pixel point to be estimated as a new seed point and determining the same phase factor value as the phase factor value of the reconstructed pixel point to be estimated;

if the reconstructed pixel point to be estimated has different phase factor values in all field maps, then resetting the reconstructed pixel point to be estimated to a pixel point to be estimated and determining the different phase factor values as candidate phase factor values; and using the new seed point as a starting point and estimating the candidate phase factor values at the highest resolution by using the estimation method as described in step 13 to determine the phase factor value of the reconstructed pixel point to be estimated.

Step 16, obtaining separate images of two predetermined components according to the phase factor values of the reconstructed seed point and the reconstructed pixel point to be estimated.

After determining the phase factor values of the reconstructed seed point and the reconstructed pixel point to be estimated, the separate images of water and fat can be obtained. Since the existence of the transverse relaxation time $T_2^*$ may affect the reconstruction accuracy of the chemical shift encoding imaging, this embodiment may further include a process of correcting the chemical shift encoding imaging, and the process includes:

correcting the chemical shift coding imaging according to the reconstructed field map and a lateral relaxation time obtained by a global search based on the reconstructed field map.

By using the technical solutions provided by the present invention, the field map estimation is performed at multiple resolutions, a region simultaneously containing two components can be identified as a seed point at a low resolution, thus increasing the number and distribution range of seed points. Multiple high-resolution field maps are merged by using a self-checking mechanism, eliminating the deviation caused by a jump of the phase factor values at the highest resolution, and ensuring the correctness of selection of the final seed point, so that the signals of the two components can be accurately identified.

The method for the magnetic resonance chemical shift encoding imaging is described below in detail by means of specific embodiments:

Embodiment 1

A simplified multi-point magnetic resonance (MR) signal model of a tissue image containing two components (taking water and fat as examples in this embodiment) may be expressed as:

$$S_n = \left(\rho_w + \rho_f \sum_{p=1}^{P} \alpha_p e^{-i2\pi f_{F,p} TE_n}\right) e^{-i2\pi f_B TE_n}, n = 1, 2, \ldots N, N \geq 3$$

where $S_n$ represents the signal intensity at the echo time $TE_n$, N represents the number of echoes, and N≥3 may be selected in this embodiment; $\rho_w$ and $\rho_f$ represent the intensity values of water and fat, respectively, and are complex numbers; fat contains P peak components, the relative amplitude corresponding to each component is $\alpha_p$, satisfying $$\sum_{p=1}^{P} \alpha_p = 1,$$

and $f_{F,p}$ represents the chemical shift of the $p^{th}$ peak component with respect to water; and $f_B$ represents the local field of $B_0$. To avoid phase unwrapping, a phase factor (phasor) $p_B$ is introduced in this embodiment:

$$p_B = e^{i2\pi f_B \Delta TE} = e^{i\Phi_B}$$

where $\Delta TE = TE_2 - TE_1$; and $\Phi_B$ represents the phase of $p_B$, having the range of $[-\pi, \pi]$ and referring to the phase accumulation due to $f_B$ in the $\Delta TE$ time.

It can be known from the above formula that $p_B$ is a periodic function about $f_B$, and different $f_B$s with the same $p_B$ can obtain the same result in the water-fat image reconstruction process. Therefore, in this embodiment, the actual $B_0$ local field $f_B$ is not estimated, only the estimated phase factor $p_B$ is obtained, which also characterizes the non-uniformity of the $B_0$ local field, and is called a field map in this embodiment.

It can be seen from the above formula that the phase factor $p_B$ can be obtained by estimating $\Phi_B$ within $[-\pi, \pi]$. According to a variable projection (VARPRO) method, a least square method can be used to solve $\Phi_B$:

$$\Phi_B = \mathrm{argmin} \, err(\Phi_B) = \mathrm{argmin} \|(I - AA^+)\psi(\Phi_B)S\|$$

where $S = [S_1, S_2, \cdots, S_N]^T$, $A = [A_1; A_2; \ldots ; A_N]$, $$A_n = \left[1 \sum_{p=1}^{P} \alpha_p e^{-i2\pi f_{F,p} TE_n}\right],$$

$A^+ = (A^T A)^{-1} A^T, \psi(\Phi_B) = \mathrm{diag}\left(1, e^{i\Phi_B}, \ldots, e^{i\frac{(TE_N - TE_1)}{\Delta TE}\Phi_B}\right),$ and I is a N×N matrix.

$err(\Phi_B)$ describes the relationship between the phase $\Phi_B$ of the phase factor $p_B$ and the fitting error, and represents a phasor-error spectrum, which is defined as a corresponding model fitting error under different phase factor values. The local minimum value of $err(\Phi_B)$ characterizes a phase factor value corresponding to the pixel, and for most pixel points, the number of their phase factor values is not only one.

Figure 2:
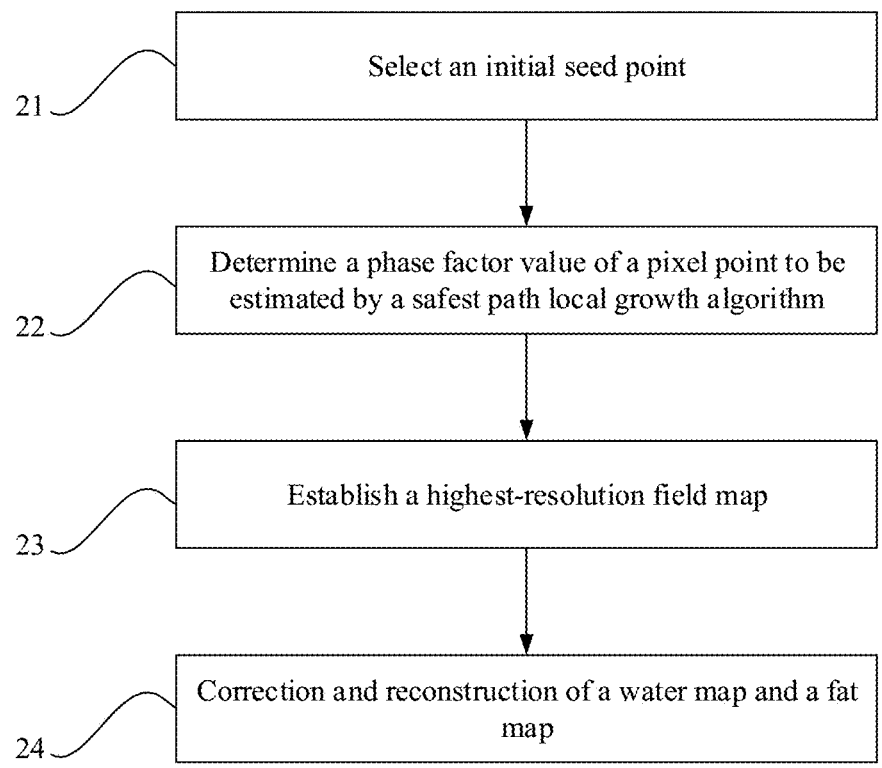
FIG. 2 shows a flowchart of a self-checking field map estimation method based on multi-resolution safest path local growth by way of example.

In order to select the correct phase factor value from a plurality of pixel points, this embodiment provides a self-checking field map estimation method based on multi-resolution safest path local growth, which realizes the correct selection of the phase factor value. As shown in FIG. 2, the method includes:

Step 21, selecting an initial seed point.

In this embodiment, a two-dimensional original image is low-pass filtered and the original image is under-sampled according to a pre-defined under-sampling coefficient to obtain two-dimensional original images at different low resolutions. For example, the under-sampling coefficients can be determined as [3 3], [5 5], [16 8], and [8 16], and then four sets of original images at low resolutions can be obtained. For each pixel point in each image at a low resolution, its phasor-error spectrum is depicted, and a phase factor value that causes the pixel point to reach a local minimum value is determined according to the phasor-error spectrum. If the pixel point satisfies the following two conditions, then it can be determined as a seed point:

(1) having a signal-to-noise ratio greater than a predetermined value: m>th, where m represents an amplitude of the pixel point, and th represents a signal-to-noise ratio threshold value.

(2) having a unique phase factor value: the maximum and minimum values of the phasor-error spectrum are represented by $A_{max}$ and $A_{min}$, respectively, and the fitting error multiple is represented by a, then the threshold value can be set to be $A_{min} + \alpha^*(A_{max} - A_{min})$. If there is only one local minimum value that causes the fitting error to be less than the threshold value, then the corresponding pixel point is considered to have a unique phase factor value; otherwise, other local solutions of the pixel point smaller than the threshold value simultaneously remain, and then the pixel point has a plurality of phase factor values.

The amplitude m of the pixel point may be obtained by many calculation methods, for example:

$m = \max\{abs(S_1), abs(S_2), \ldots, abs(S_N)\}$, $m = abs(S_1) + abs(S_2) + abs(S_N)$ or the like.

For the selection of th and $\alpha$, it is necessary to exclude seed points with low SNRs and a plurality of minimum solutions, and to ensure that enough seed points are obtained. One candidate value may be obtained as follows: th is equal to 0.2 times the 98th percentile value of all pixel amplitudes, and $\alpha$ is 0.4.

Figure 3:
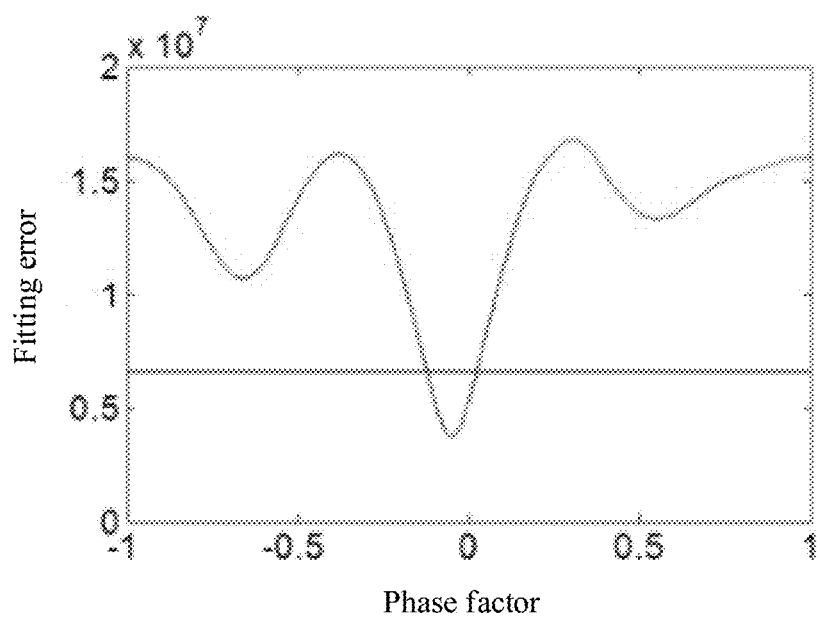
FIG. 3 shows a phasor-error spectrum of one seed point by way of example, wherein the abscissa represents a phase factor (phasor), the ordinate represents a corresponding fitting error (err$\Phi_B(\pi)$, dimensionless), and in this figure, the straight line represents a threshold, and the curve line represents the fitting error.

FIG. 3 shows a phasor-error spectrum of one seed point, and the one seed point has only one phase factor value. For the remaining pixel points with more than one phase factor value (referred to a pixel point to be estimated in this embodiment, and its multiple phase factor values are collectively referred to as candidate phase factor values), a correct solution needs to be selected from the following steps.

Optionally, in this step, seed points are selected for the above four sets of low-resolution images. It should be noted that the above four sets of low-resolution images are merely examples. If other low-resolution images are applicable to the present invention, they should also be included in the protection scope of the present invention, and are included herein by reference.

Step 22, determining the phase factor value of the pixel point to be estimated by the safest path local growth algorithm.

Based on the initial seed point, this embodiment uses the following local growth algorithm to complete the phase factor estimation of the pixel point to be estimated. Its process may include: selecting a candidate value having the maximum similarity to phase factor values of adjacent seed points from the candidate phase factor values of the pixel point to be estimated as a phase factor value of the current pixel point to be estimated, namely:

$p_B = \arg\max\{D_1, D_2, \ldots, D_S\}$, where $D_s$ represents the phasor similarity and is defined as:

$$D_s = \frac{\sum_{k=1}^{K} m_k \cos(\text{angle}(p_{B,s} * \text{conj}(p_{B,k})))}{\sum_{k=1}^{K} m_k}$$

where K represents the number of seed points within eight neighborhoods of the current pixel point to be estimated (if the current pixel point to be estimated and its adjacent area are divided into a three-by-three format, then eight adjacent areas other than the area where the current pixel point to be estimated is located are the eight neighborhoods); $m_k$ represents an amplitude of the $k^{th}$ seed point, and the corresponding phase factor value is $p_{B,k}$, where $p_{B,s}$ represents one candidate phase factor value of the current pixel point to be estimated; conj(.) represents taking a complex conjugate; and angle(.) represents taking an angle.

Figure 4:
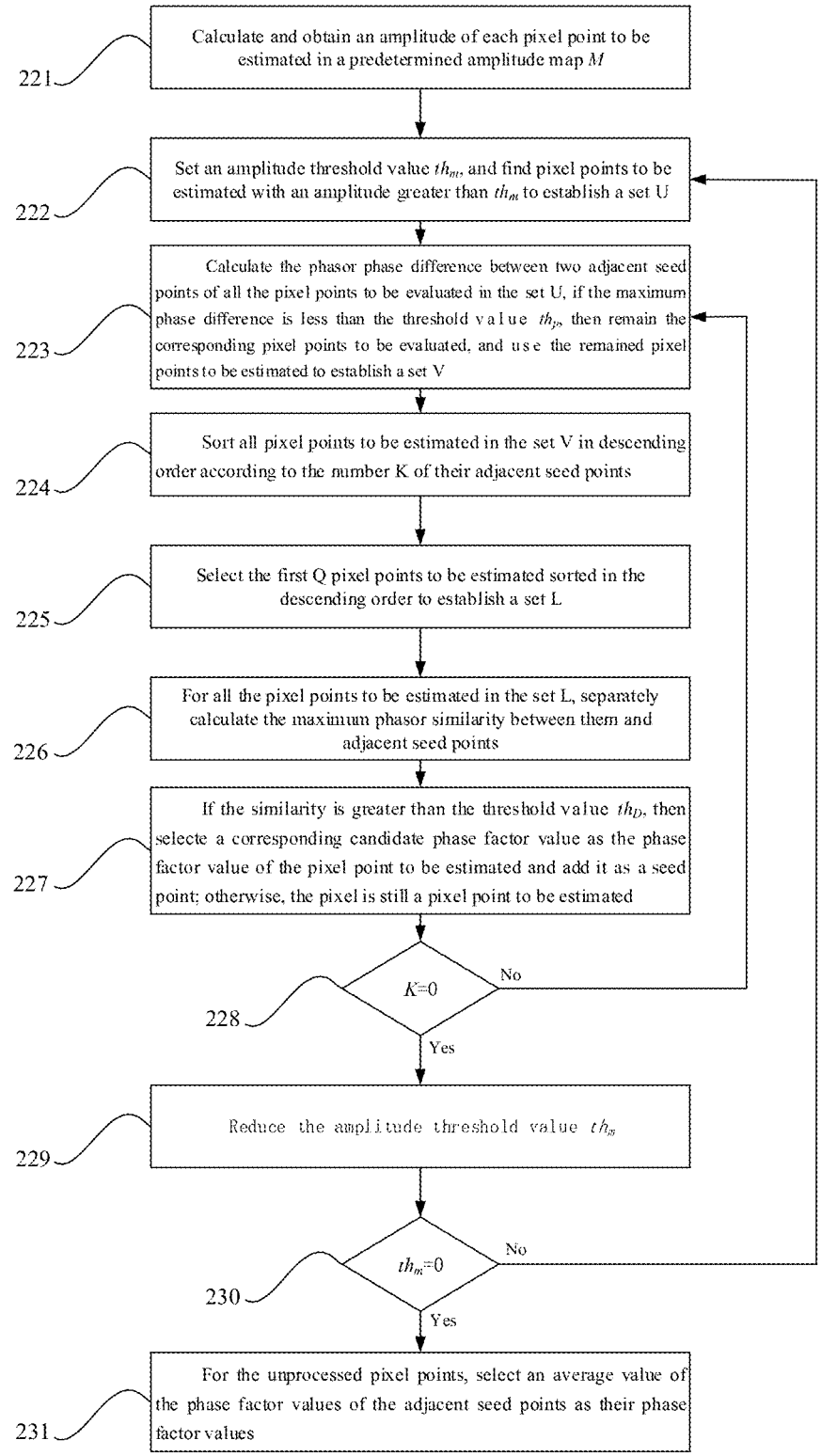
FIG. 4 shows a flowchart of a safest path local growth algorithm by way of example.

Optionally, as shown in FIG. 4, the safest path local growth algorithm provided in this embodiment is as follows:

step 221, calculating to obtain an amplitude of each pixel point to be estimated from the predetermined amplitude map M;

step 222, setting the amplitude threshold value $th_m$, and finding pixel points to be estimated with the amplitude greater than $th_m$ to establish the set U;

step 223, calculating the phasor phase difference between two adjacent seed points of all the pixel points to be evaluated in the set U, if the maximum phase difference is less than the threshold value $th_p$, then remaining the corresponding pixel points to be evaluated, and using the remained pixel points to be estimated to establish the set V; and if the maximum phase difference is greater than the threshold value $th_p$, then removing the corresponding pixel points to be estimated;

step 224, sorting all pixel points to be estimated in the set V in descending order according to the number K of their adjacent seed points;

step 225, selecting the first Q pixel points to be estimated sorted in the descending order to establish the set L;

step 226, for all the pixel points to be estimated in the set L, separately calculating the maximum phasor similarity between them and adjacent seed points;

step 227, if the similarity is greater than the threshold value $th_D$, then selecting a corresponding candidate phase factor value as the phase factor value of the pixel point to be estimated and adding it as a seed point; otherwise, this pixel point is still a pixel point to be estimated;

step 228, repeating steps 223 to 227 until K=0;

step 229, reducing the amplitude threshold value $th_m$;

step 230, repeating steps 222 to 229 until the amplitude threshold value $th_m=0$; and step 231, for the unprocessed pixel points to be estimated in steps 223 and 227, selecting an average value of the phase factor values of the adjacent seed points as their phase factor values.

The above safest path local growth algorithm is performed separately at each low resolution.

The amplitude of each pixel point in the amplitude map M may be defined as $m=\max\{abs(S_1), abs(S_2), \ldots, abs(S_N)\}$, $m=abs(S_1)+abs(S_2)+abs(S_N)$ or the like; there may be multiple methods for selecting the amplitude threshold $th_m$, for example, selecting according to the percentile values of all pixel amplitudes. The threshold value $th_D$ and threshold value $th_p$ may be determined according to the smoothness of the candidate field map, such as selecting 0.9 and $\pi/2$. The adjacent seed points of the pixel point to be estimated may be defined as the seed points within its four or eight neighborhoods; and the Q value may be selected to be equal to ¼ of the number of pixel points to be estimated in the set V.

Step 23, establishing the highest-resolution field map.

The low-resolution field map obtained by the safest path local growth algorithm in step 22 is used as an initial value to select a field map at the highest resolution, which is called field map mapping in this embodiment. Its implementation process may include: calculating the phasor similarity between all candidate phase factor values of each pixel point at the highest resolution and the phase factor values of the pixel point at a lower resolution corresponding thereto, wherein the candidate value with the highest similarity is the phase factor value of the current pixel point.

In this embodiment, the selection of the seed points and the estimation of the local growth algorithm are performed at a plurality of different low resolutions. Therefore, a plurality of field maps at the highest resolution is also obtained in this step. Then, the plurality of field maps described above is merged by using a self-checking mechanism to obtain a field map. Its implementation process may include: if one pixel point has the same phase factor value in all the field maps, then selecting the pixel point as a new seed point; and if one pixel point has different values in all the field maps, then resetting the pixel point as a pixel point to be estimated, wherein the phase factor value of the pixel point to be estimated is one of the candidate phase factor values.

The above safest path local growth algorithm is used to complete the selection of the phase factor value of the pixel point to be estimated at the highest resolution with the new seed point as a starting point to obtain a final field map. The principle of this step is the same as the local growth algorithm at low resolutions described above, so it is not repeated in this embodiment.

Step 24, performing a correction and reconstruction of a water map and a fat map.

The existence of the transverse relaxation time $T_2^*$ may affect the reconstruction accuracy of the water map and fat map, so this step is to correct $T_2^*$. In general, the correction of $T_2^*$ is not related to the estimation of the field map, and there is no multi-extreme phenomenon in the estimation of $T_2^*$. Therefore, based on the completion of the field map estimation, the following formula is solved to obtain the minimum value of $T_2^*$ by a global search:

$$T_2^* = \arg\min\|(I-EA(EA)^+\psi(\Phi_B)S\|$$

where $E=\text{diag}(e^{-T_2^*/TE_1}, e^{-T_2^*/TE_2}, \ldots, e^{-T_2^*/TE_N})$. Using the obtained field map and $T_2^*$, the water map and fat map are then calculated by the following formula:

$$\begin{bmatrix} W \\ F \end{bmatrix} = (EA)^+\psi(\Phi_B)\hat{S}$$

where W and F are the obtained water map and fat map after calculating, respectively, and are complex numbers.

Figure 7:
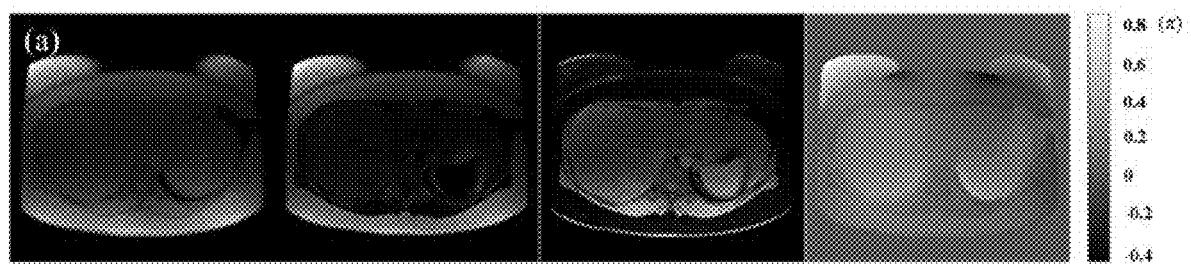
FIG. 7 is an example diagram of abdominal water-fat separation for verifying a method for magnetic resonance chemical shift encoding imaging according to embodiment 1, wherein, from left to right in this figure are an original image, a separated fat map, a separated water map, and an estimated field diagram in order.
Figure 8:
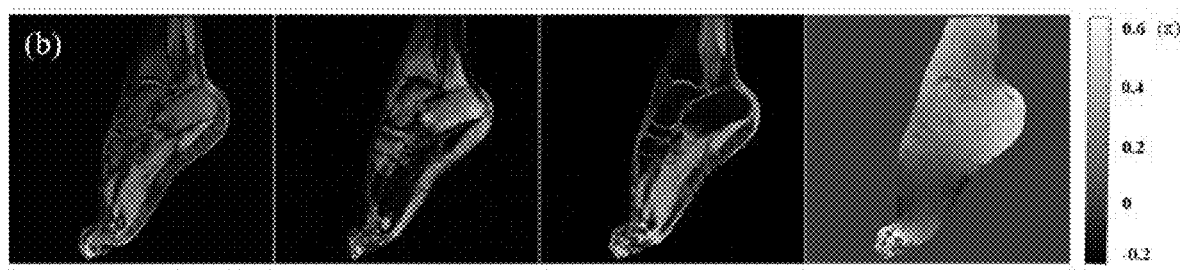
FIG. 8 is an example diagram of ankle water-fat separation for verifying a method for magnetic resonance chemical shift encoding imaging according to embodiment 1, wherein, from left to right in this figure are an original image, a separated fat map, a separated water map, and an estimated field diagram in order.

To verify the feasibility of the method for the magnetic resonance chemical shift encoding imaging provided in this embodiment, the following tests are performed in experiments with two kinds of body tissue, wherein the test objects are an abdomen and an ankle, respectively. For the abdomen, the echo time TE=1.208/3.212/5.216/7.220/9.224/11.228 ms (equal spacing), the matrix size=256×256×5, the main magnetic field $B_0$=1.5 T. For the ankle, the echo time TE=1.356/3.672/4.444/7.532 ms (unequal spacing), the matrix size=256×256×2, and the main magnetic field $B_0$=3 T. The processing environment of the experimental data is a workstation with Intel E5-2650 v2 CPU and 64 GB RAM. The data processing software used is MATLAB. FIGS. 7 and 8 show separation results based on one layer of the abdomen and the ankle. It can be seen that in the body tissue experiments, there is no obvious wrong tissue in the obtained water map and fat map.

It should be noted that the method for the magnetic resonance chemical shift encoding imaging provided by the present invention can be used not only for water-fat separation imaging, but also for applications of separating other chemical shift components, and the difference among them is only the corresponding chemical shift values input in a simplified MR signal model containing two components.

The method for the magnetic resonance chemical shift encoding imaging provided in this embodiment also has high robustness in areas with low signal-to-noise ratios. The multi-resolution field map estimation and local growth estimation strategies are used. Compared with the traditional single-resolution local growth algorithms, an area simultaneously containing both water and fat can be identified as a seed point at a low resolution, increasing the number and distribution range of seed points. The field map estimation and local growth at low resolutions are independent, that is, there are no overlaps in the processing between the individual low resolutions, which eliminates an impact of a jump of the phase factor value that may exist between different resolutions. The self-checking mechanism is used to merge multiple high-resolution field maps, which eliminates the deviation caused by a jump of the phase factor value at the highest resolution and ensures the correctness of the final seed point selection. After an algorithm optimization, the method provided in this embodiment has higher operating efficiency.

Figure 5:
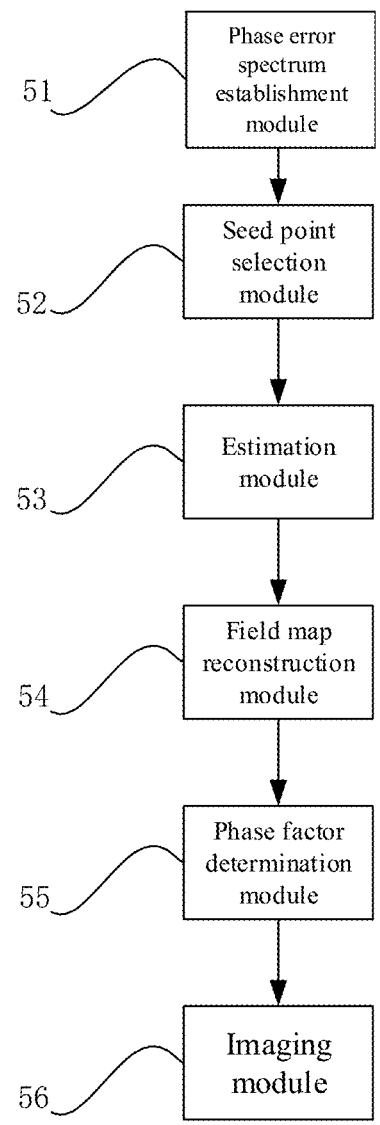
FIG. 5 shows a structural diagram of an apparatus for magnetic resonance chemical shift encoding imaging by way of example.

The present invention further proposes an apparatus for magnetic resonance chemical shift encoding imaging. As shown in FIG. 5, the apparatus includes:

the phase error spectrum establishment module 51, configured for establishing a phasor-error spectrum based on a simplified multi-point magnetic resonance signal model in a sample image at a predetermined resolution;

the seed point selection module 52, configured for determining a pixel point having a unique phase factor value and causing the phasor-error spectrum to reach a local minimum value in the phasor-error spectrum as an initial seed point;

the estimation module 53, configured for estimating a phase factor value of a pixel point to be estimated according to the initial seed point to obtain a field map at the predetermined resolution;

the field map reconstruction module 54, configured for mapping a plurality of field maps at the predetermined resolution separately at the highest resolution to obtain a plurality of field maps at the highest resolution, and merging the plurality of field maps to obtain a reconstructed field map;

the phase factor determination module 55, configured for determining a reconstructed seed point from the reconstructed field map, and estimating based on the reconstructed seed point to obtain a phase factor value of a reconstructed pixel point to be estimated; and the imaging module 56, configured for obtaining separate images of two predetermined components according to the phase factor values of the reconstructed seed point and the reconstructed pixel point to be estimated.

Optionally, the seed point selection module 52 includes:

a minimum value determination sub-module, configured for obtaining a phasor-error spectrum of each pixel point in the image at the predetermined resolution, and determining a phase factor value causing the pixel point to reach a local minimum value according to the phasor-error spectrum; and a seed point determination sub-module, configured for if a signal-to-noise ratio of the pixel point is greater than a predetermined value and has a unique phase factor value, determining the pixel point as an initial seed point.

The seed point determination sub-module may be used for if the pixel point has only one local minimum value allowing the fitting error to be less than a predetermined value, determining the local minimum value as the unique phase factor value of the pixel point.

Optionally, the estimation module 53 includes:

a first set establishment sub-module, configured for selecting a pixel point to be estimated with an amplitude greater than a first threshold value to establish a first pixel point set to be estimated;

a second set establishment sub-module, configured for obtaining a phase difference between two adjacent seed points of each pixel point to be estimated in the first pixel point set to be estimated, and selecting a pixel point to be estimated with the maximum phase difference less than a second threshold value to establish a second pixel point set to be estimated;

a third set establishment sub-module, configured for sorting pixel points to be estimated in the second pixel point set to be estimated in a descending order according to the number of the adjacent seed points, and selecting a predetermined number of pixel points to be estimated to establish a third pixel point set to be estimated;

a first phase factor determination sub-module, configured for obtaining the maximum phase similarity between a pixel point to be estimated in the third pixel set to be estimated and the adjacent seed points, and using a phase factor value of the pixel point to be estimated with the similarity greater than a third threshold value as the phase factor value of the pixel point to be estimated; and a first estimation sub-module, configured for adding the pixel point to be estimated with the similarity greater than the third threshold value as a seed point to estimate the pixel point to be estimated in the first pixel point set to be estimated until the number of adjacent seed points of the pixel point to be estimated in the first pixel point set to be estimated is zero;

a fourth set establishment sub-module, configured for determining a fourth pixel point set to be estimated by reducing the first threshold value by a predetermined amount;

a second phase factor determination sub-module, configured for determining a phase factor value of a pixel point to be estimated in the fourth pixel point set to be estimated until the first threshold value is reduced to zero; and a third phase factor determination sub-module, configured for determining the phase factor value of the pixel point to be estimated in which the phase factor value has not been determined in the first pixel point set to be estimated as an average value of the phase factor values of the adjacent seed points.

Optionally, the field map reconstruction module 54 includes:

a fourth phase factor determination sub-module, configured for obtaining phase similarity between all phase factor values of each reconstructed pixel point to be estimated at the highest resolution and a phase factor value of a corresponding pixel point at the predetermined resolution, and determining the phase factor value with the highest similarity as the phase factor value of the reconstructed pixel point to be estimated.

Optionally, the phase factor determination module 55 includes:

a fifth phase factor determination sub-module, configured for if the reconstructed pixel point to be estimated has the same phase factor value in all field maps, determining the reconstructed pixel point to be estimated as a new seed point and determining the same phase factor value as the phase factor value of the reconstructed pixel point to be estimated;

a sixth phase factor determination sub-module, configured for if the reconstructed pixel point to be estimated has different phase factor values in all field maps, resetting the reconstructed pixel point to be estimated to a pixel point to be estimated and determining the different phase factor values as candidate phase factor values; and a seventh phase factor determination sub-module, configured for estimating the candidate phase factor value at the highest resolution with the new seed point as a starting point to determine a phase factor value of the reconstructed pixel point to be estimated.

By using the apparatus for the magnetic resonance chemical shift encoding imaging provided by the present invention, the field map estimation is performed at multiple resolutions, an area simultaneously containing two components can be identified as a seed point at a low resolution, thus increasing the number and distribution range of seed points. Multiple high-resolution field maps are merged by using a self-checking mechanism, eliminating the deviation caused by a jump of the phase factor values at the highest resolution, and ensuring the correctness of selection of the final seed point, so that the signals of the two components can be accurately identified.

The present invention further provides a computer device. The computer device includes a processor and a memory storing computer-readable instructions, and the processor is configured to execute the method as described in embodiment 1 by executing the computer-readable instructions.

Figure 6:
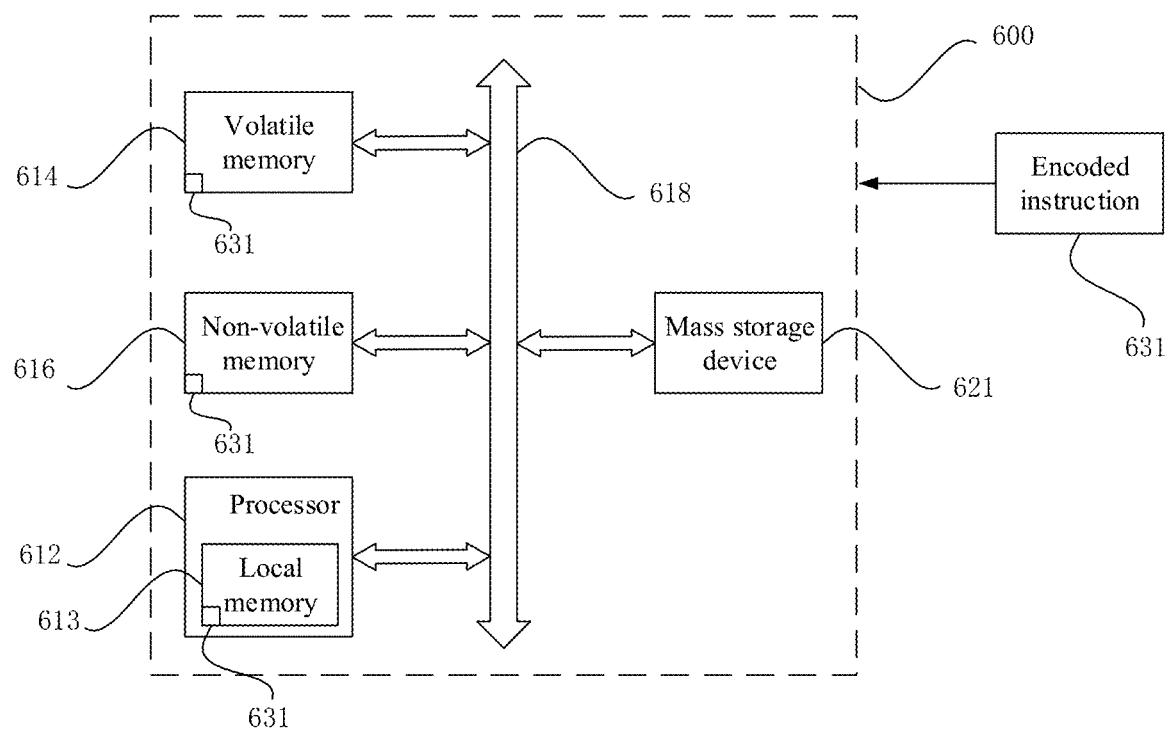
FIG. 6 shows a structural diagram of a computer device by way of example.

FIG. 6 is a block diagram of the exemplary processor platform 600 capable of executing the instruction flow shown in FIG. 4 and using the exemplary device for the magnetic resonance chemical shift encoding imaging of FIG. 5. The processor platform 600 may be a server, a personal computer, or any other type of computing device.

The processor platform 600 shown in FIG. 6 includes the processor 612. For example, the processor 612 may be implemented by one or more microprocessors or controllers from any desired home or manufacturer.

The processor 612 includes the local memory 613 (e.g. a cache memory), and communicates with a main memory via the bus 618. The main memory includes the volatile memory 614 and the non-volatile memory 616. The volatile memory 614 may be implemented by a synchronous dynamic random access memory (SDRAM), a dynamic random access memory (DRAM), a RAM bus (RAMBUS) dynamic random access memory (RDRAM), and/or any other type of random access memory device. The non-volatile memory 616 may be implemented by a flash memory and/or any other desired type of storage device. Access to the volatile memory 614 and the non-volatile memory 616 is controlled by a memory controller.

The processor platform 600 may further include one or more mass storage devices 621 for storing software and data. Examples of the mass storage devices 621 include a floppy disk drive, a hard disk drive, an optical disk drive, and a digital versatile disk (DVD) drive. The encoded instruction 631 shown in FIG. 6 may be stored on the mass storage device 621, the volatile memory 614, the non-volatile memory 616, and/or a removable storage medium such as a CD or DVD.

The present specific implementation is a clear and complete description of the technical solutions of the present invention, and the embodiments therein are only a part of the present invention, and not all of the embodiments. All other embodiments obtained by those skilled in the art based on the embodiments in the present invention without creative efforts are within the protection scope of the present invention.

What is claimed is:

1. A method for magnetic resonance chemical shift encoding imaging, comprising:
    in a sample image at a predetermined resolution, establishing a phase factor-fitting error spectrum (phasor-error spectrum) based on a simplified multi-point magnetic resonance signal model;
    determining a first pixel point as an initial seed point, wherein the first pixel point has a unique phase factor value and causes the phasor-error spectrum to reach a local minimum value in the phasor-error spectrum;
    estimating a phase factor value of a second pixel point according to the initial seed point to obtain a first plurality of field maps at the predetermined resolution;
    mapping the first plurality of field maps at the predetermined resolution separately at a highest resolution to obtain a second plurality of field maps at the highest resolution, and merging the second plurality of field maps to obtain a reconstructed field map;
    determining a reconstructed seed point in the reconstructed field map, and estimating based on the reconstructed seed point to obtain a phase factor value of a reconstructed pixel point to be estimated; and
    obtaining separate images of two predetermined components according to a phase factor value of the reconstructed seed point and the phase factor value of the reconstructed pixel point to be estimated.

2. The method of claim 1, wherein the step of determining the first pixel point as the initial seed point comprises:
    obtaining the phasor-error spectrum of each pixel point in the sample image at the predetermined resolution, and determining the unique phase factor value causing the first pixel point to reach the local minimum value according to the phasor-error spectrum; and
    if a signal-to-noise ratio of the first pixel point is greater than a first predetermined value and has the unique phase factor value, determining the first pixel point as the initial seed point.

3. The method of claim 2, wherein determining the first pixel point having the unique phase factor value comprises:
    if the first pixel point has only one local minimum value causing a fitting error to be less than a second predetermined value, determining the only one local minimum value as the unique phase factor value of the first pixel point.

4. The method of claim 3, wherein the step of estimating the phase factor value of the second pixel point according to the initial seed point comprises:
    if the second pixel point includes a plurality of local minimum values, determining the plurality of local minimum values with fitting errors less than a third predetermined value as a plurality of sub-phase factor values of the second pixel point; and selecting a phase factor value having a maximum similarity to phase factor values of adjacent seed points from the plurality of sub-phase factor values of the second pixel point as the phase factor value of the second pixel point.

5. The method of claim 4, wherein the step of estimating the phase factor value of the second pixel point according to the initial seed point comprises:
selecting pixel points to be estimated with amplitudes greater than a first threshold value to establish a first pixel point set to be estimated;
obtaining a phase difference between adjacent seed points of each pixel point to be estimated in the first pixel point set to be estimated, and selecting pixel points to be estimated with maximum phase differences less than a second threshold value to establish a second pixel point set to be estimated;
sorting the pixel points to be estimated in the second pixel point set to be estimated in a descending order according to a number of the adjacent seed points, and selecting a predetermined number of pixel points to be estimated to establish a third pixel point set to be estimated;
obtaining a maximum phase similarity between a pixel point to be estimated in the third pixel point set to be estimated and seed points adjacent to the pixel point to be estimated in the third pixel point set to be estimated, and using a phase factor value of the pixel point to be estimated with the maximum phase similarity greater than a third threshold value as the phase factor value of the pixel point to be estimated; and
adding the pixel point to be estimated with the maximum phase similarity greater than the third threshold value as a seed point to estimate the pixel points to be estimated in the first pixel point set to be estimated until the number of adjacent seed points of the pixel points to be estimated in the first pixel point set to be estimated is zero.

6. The method of claim 5, wherein the step of estimating the phase factor value of the second pixel point according to the initial seed point further comprises:
reducing the first threshold value by a predetermined amount to determine a fourth pixel point set to be estimated, and determining a phase factor values of a pixel points to be estimated in the fourth pixel point set to be estimated until the first threshold value is reduced to zero; and
determining phase factor values of the pixel points to be estimated without determining the phase factor values in the first pixel point set to be estimated as an average value of the phase factor values of the adjacent seed points.

7. The method of claim 1, wherein the step of mapping the first plurality of field maps at the predetermined resolution separately at the highest resolution comprises:
obtaining a phase similarity between all phase factor values of the reconstructed pixel point to be estimated at the highest resolution and the phase factor value of the pixel point at the predetermined resolution corresponding to the reconstructed pixel point, and determining a phase factor value with a highest phase similarity as the phase factor value of the reconstructed pixel point to be estimated.

8. The method of claim 7, wherein determining the phase factor value of the reconstructed pixel point to be estimated comprises:

if the reconstructed pixel point to be estimated has a same phase factor value in all the second plurality of field maps, determining the reconstructed pixel point to be estimated as a new seed point and determining the same phase factor value as the phase factor value of the reconstructed pixel point to be estimated; and
if the reconstructed pixel point to be estimated has different phase factor values in all the second plurality of field maps, resetting the reconstructed pixel point to be estimated to be a pixel point to be estimated and determining the different phase factor values as candidate phase factor values.

9. The method of claim 8, wherein the step of determining the phase factor value of the reconstructed pixel point to be estimated further comprises:
estimating the candidate phase factor values at the highest resolution with the new seed point as a starting point to determine the phase factor value of the reconstructed pixel point to be estimated.

10. The method of claim 1, further comprising:
correcting the magnetic resonance chemical shift encoding imaging according to the reconstructed field map and a transverse relaxation time obtained by a global search based on the reconstructed field map.

11. An apparatus for magnetic resonance chemical shift encoding imaging, comprising:
a phase error spectrum establishment module, configured for establishing a phase factor-fitting error spetrum (phasor-error spectrum) based on a simplified multi-point magnetic resonance signal model in a sample image at a predetermined resolution;
a seed point selection module, configured for determining a first pixel point as an initial seed point, wherein the first pixel point has a unique phase factor value and causes the phasor-error spectrum to reach a local minimum value in the phasor-error spectrum;
an estimation module, configured for estimating a phase factor value of a second pixel point according to the initial seed point to obtain a first plurality of field maps at the predetermined resolution;
a field map reconstruction module, configured for mapping the first plurality of field maps at the predetermined resolution separately at a highest resolution to obtain a second plurality of field maps at the highest resolution, and merging the second plurality of field maps to obtain a reconstructed field map;
a phase factor determination module, configured for determining a reconstructed seed point in the reconstructed field map, and estimating based on the reconstructed seed point to obtain a phase factor value of a reconstructed pixel point to be estimated; and
an imaging module, configured for obtaining separate images of two predetermined components according to a phase factor value of the reconstructed seed point and the phase factor value of the reconstructed pixel point to be estimated.

12. The apparatus of claim 11, wherein the seed point selection module comprises:
a minimum value determination sub-module, configured for obtaining the phasor-error spectrum of each pixel point in the sample image at the predetermined resolution, and determining the unique phase factor value causing the first pixel point to reach the local minimum value according to the phasor-error spectrum; and
a seed point determination sub-module, configured for if a signal-to-noise ratio of the first pixel point is greater than a first predetermined value and has the unique phase factor value, determining the first pixel point as the initial seed point.

13. The apparatus of claim 12, wherein the seed point determination sub-module is configured for if the first pixel point has only one local minimum value causing a fitting error to be less than a second predetermined value, determining the only one local minimum value as the unique phase factor value of the first pixel point.

14. The apparatus of claim 13, wherein the estimation module comprises:
a first set establishment sub-module, configured for selecting pixel points to be estimated with amplitudes greater than a first threshold value to establish a first pixel point set to be estimated;
a second set establishment sub-module, configured for obtaining a phase difference between adjacent seed points of each pixel point to be estimated in the first pixel point set to be estimated, and selecting pixel points to be estimated with maximum phase differences less than a second threshold value to establish a second pixel point set to be estimated;
a third set establishment sub-module, configured for sorting pixel points to be estimated in the second pixel point set to be estimated in a descending order according to a number of the adjacent seed points, and selecting a predetermined number of pixel points to be estimated to establish a third pixel point set to be estimated;
a first phase factor determination sub-module, configured for obtaining the a maximum phase similarity between a pixel point to be estimated in the third pixel point set to be estimated and seed points adjacent to the pixel point to be estimated in the third pixel point set to be estimated, and using a phase factor value of the pixel point to be estimated with the maximum phase similarity greater than a third threshold value as the phase factor value of the pixel point to be estimated; and
a first estimation sub-module, configured for using the pixel point to be estimated with the maximum phase similarity greater than the third threshold value as a new seed point to estimate the pixel points to be estimated in the first pixel point set to be estimated until the number of adjacent seed points of the pixel points to be estimated in the first pixel point set to be estimated is zero.

15. The apparatus of claim 14, wherein the estimation module further comprises:
a fourth set establishment sub-module, configured for determining a fourth pixel point set to be estimated by reducing the first threshold value by a predetermined amount;
a second phase factor determination sub-module, configured for determining a phase factor values of pixel points to be estimated in the fourth pixel point set to be estimated until the first threshold value is reduced to zero; and
a third phase factor determination sub-module, configured for determining the phase factor values of the pixel points to be estimated without determining the phase factor values in the first pixel point set to be estimated as an average value of the phase factor values of the adjacent seed points.

16. The apparatus of claim 11, wherein the field map reconstruction module comprises:
a fourth phase factor determination sub-module, configured for obtaining a phase similarity between all phase factor values of the reconstructed pixel point to be estimated at the highest resolution and the phase factor value of the pixel point at the predetermined resolution corresponding to the reconstructed pixel point, and determining a phase factor value with a highest phase similarity as the phase factor value of the reconstructed pixel point to be estimated.

17. The apparatus of claim 16, wherein the phase factor determination module comprises:
a fifth phase factor determination sub-module, configured for if the reconstructed pixel point to be estimated has a same phase factor value in all the second plurality of field maps, determining the reconstructed pixel point to be estimated as a new seed point and determining the same phase factor value as the phase factor value of the reconstructed pixel point to be estimated;
a sixth phase factor determination sub-module, configured for if the reconstructed pixel point to be estimated has different phase factor values in all the second plurality of field maps, resetting the reconstructed pixel point to be estimated to be a pixel point to be estimated and determining the different phase factor values as candidate phase factor values; and
a seventh phase factor determination sub-module, configured for estimating the candidate phase factor values at the highest resolution with the new seed point as a starting point, to determine the phase factor value of the reconstructed pixel point to be estimated.

18. A non-transitory computer-readable storage medium, comprising: a computer instruction, wherein when the computer instruction is executed, the method of claim 1 is executed.

19. A device, comprising:
a processor; and
a non-transitory memory storing computer-readable instructions, wherein the processor is configured to execute the method of claim 1 by executing the computer-readable instructions.

* * * * *